United States Patent
Weightman et al.

(10) Patent No.: US 8,122,759 B2
(45) Date of Patent: Feb. 28, 2012

(54) DETERMINING FLUID RHEOLOGICAL PROPERTIES

(75) Inventors: Glenn H. Weightman, Duncan, OK (US); Bruce C. Lucas, Marlow, OK (US)

(73) Assignee: Halliburton Energy Services Inc.,, Duncan, OK (US)

( * ) Notice: Subject to any disclaimer, the term of this patent is extended or adjusted under 35 U.S.C. 154(b) by 13 days.

(21) Appl. No.: 12/914,571

(22) Filed: Oct. 28, 2010

(65) Prior Publication Data

US 2011/0036584 A1 Feb. 17, 2011

Related U.S. Application Data

(62) Division of application No. 11/868,399, filed on Oct. 5, 2007, now Pat. No. 7,832,257.

(51) Int. Cl.
*G01N 11/08* (2006.01)
(52) U.S. Cl. ..................................... 73/54.09
(58) Field of Classification Search .................. 73/54.09
See application file for complete search history.

(56) References Cited

U.S. PATENT DOCUMENTS

| | | | |
|---|---|---|---|
| 3,102,548 A | 9/1963 | Smith et al. | |
| 3,254,719 A | 6/1966 | Root | |
| 3,654,994 A * | 4/1972 | Slagel et al. | 166/308.4 |
| 3,730,275 A | 5/1973 | McClaflin et al. | |
| 3,758,406 A | 9/1973 | Malone et al. | |
| 4,152,274 A | 5/1979 | Phillips et al. | |
| 4,519,239 A | 5/1985 | Kiesewetter et al. | |
| 4,574,622 A | 3/1986 | Hatfield | |
| 4,574,624 A | 3/1986 | Lehtinen et al. | |
| 4,583,395 A | 4/1986 | Anantaraman | |
| 4,587,837 A | 5/1986 | Newbould | |
| 4,680,957 A | 7/1987 | Dodd | |
| 4,685,328 A | 8/1987 | Huebner et al. | |
| 4,700,567 A | 10/1987 | Frey et al. | |

(Continued)

FOREIGN PATENT DOCUMENTS

EP 1403465 3/2004

(Continued)

OTHER PUBLICATIONS

U.S. Appl. No. 11/957,071, filed Dec. 14, 2007, entitled "Determining Solid Content Concentration in a Fluid Stream," Inventors Glenn H. Weightman et al. (17601-018001).

(Continued)

*Primary Examiner* — Hezron E Williams
*Assistant Examiner* — Rodney T Frank
(74) *Attorney, Agent, or Firm* — John W. Wustenberg; Fish & Richardson, P.C.

(57) ABSTRACT

Controlling a well injection operation, such as a well fracturing operation, includes identifying a flow characteristic of a fracturing fluid, identifying a flow characteristic of a base fluid used for forming the fracturing fluid, determining an amount of friction reduction change of the fracturing fluid, and adjusting the amount of friction reduction of the fracturing fluid to coincide with a selected friction reduction amount. Identifying a flow characteristic may be performed by a rheology measuring device including a measurement tube, a first pressure sensor disposed at a first position on the measurement tube, a second pressure sensor disposed at a second position on the measurement tube, a flow meter disposed at a third position along the measurement tube, a temperature sensor disposed at a fourth location along the measurement tube, and a control unit interconnected to the first and second pressure sensors, the flow meter, and the temperature sensor.

12 Claims, 8 Drawing Sheets

U.S. PATENT DOCUMENTS

| | | | |
|---|---|---|---|
| 4,726,219 A | 2/1988 | Pearson et al. |
| 4,750,351 A | 6/1988 | Ball |
| 4,793,174 A | 12/1988 | Yau |
| 4,798,081 A | 1/1989 | Hazlitt et al. |
| 4,817,416 A | 4/1989 | Blanch et al. |
| 4,821,564 A | 4/1989 | Person et al. |
| 4,901,563 A | 2/1990 | Pearson |
| 5,142,899 A | 9/1992 | Park et al. |
| 5,165,292 A | 11/1992 | Prohaska |
| 5,172,585 A | 12/1992 | Gleissle |
| 5,209,108 A | 5/1993 | Shackelford |
| 5,257,529 A | 11/1993 | Taniguchi et al. |
| 5,347,852 A | 9/1994 | Mode |
| 5,447,440 A | 9/1995 | Davis et al. |
| 5,583,284 A | 12/1996 | Martin et al. |
| 5,637,790 A | 6/1997 | De Corral |
| 5,756,883 A | 5/1998 | Forbes |
| 5,847,268 A | 12/1998 | Ball |
| 5,932,800 A | 8/1999 | Cummings et al. |
| 6,178,811 B1 | 1/2001 | Bonne et al. |
| 6,182,503 B1 | 2/2001 | Mode et al. |
| 6,196,058 B1 | 3/2001 | Chen |
| 6,220,747 B1 | 4/2001 | Gosselin |
| 6,267,002 B1 | 7/2001 | Ehwald et al. |
| 6,272,905 B1 | 8/2001 | Drzewiecki |
| 6,276,195 B1 | 8/2001 | de Corral |
| 6,311,136 B1 | 10/2001 | Henry et al. |
| 6,412,337 B1 | 7/2002 | Arzate et al. |
| 6,470,736 B2 | 10/2002 | Price |
| 6,477,891 B2 | 11/2002 | Ehwald et al. |
| 6,484,565 B2 | 11/2002 | Shin et al. |
| 6,507,791 B2 | 1/2003 | Henry et al. |
| 6,523,396 B2 | 2/2003 | Shin et al. |
| 6,561,010 B2 | 5/2003 | Wilson et al. |
| 6,561,011 B2 | 5/2003 | Collin et al. |
| 6,575,019 B1 | 6/2003 | Larson |
| 6,581,440 B1 | 6/2003 | Rupieper et al. |
| 6,584,832 B2 | 7/2003 | Petro et al. |
| 6,705,161 B1 | 3/2004 | Klassen |
| 6,708,553 B2 | 3/2004 | Bures |
| 6,732,573 B2 | 5/2004 | Shin et al. |
| 6,745,615 B2 | 6/2004 | Kensey et al. |
| 6,755,079 B1 | 6/2004 | Proett et al. |
| 6,779,382 B2 | 8/2004 | Rupieper et al. |
| 6,796,168 B1 | 9/2004 | Goldstein et al. |
| 6,877,361 B2 | 4/2005 | Bures |
| 6,898,963 B2 | 5/2005 | Irani |
| 6,907,772 B2 | 6/2005 | Kensey et al. |
| 6,923,055 B2 | 8/2005 | Klassen |
| 6,941,797 B2 | 9/2005 | Nowak |
| 7,024,921 B2 | 4/2006 | Sutton |
| 7,096,744 B2 | 8/2006 | Kielb et al. |
| 7,111,499 B2 | 9/2006 | Keen |
| 7,302,863 B2 | 12/2007 | Kielb et al. |
| 7,543,596 B2 | 6/2009 | Laverdiere et al. |
| 7,832,257 B2 * | 11/2010 | Weightman et al. ......... 73/54.09 |
| 2005/0173003 A1 | 8/2005 | Laverdiere et al. |
| 2006/0088425 A1 | 4/2006 | Lucas et al. |
| 2006/0096754 A1 | 5/2006 | Weightmann |

FOREIGN PATENT DOCUMENTS

| | | |
|---|---|---|
| WO | WO 02/23010 | 3/2002 |

OTHER PUBLICATIONS

Foreign communication related to a counterpart application dated Mar. 20, 2009.

Notification of Transmittal of the International Search Report and the Written Opinin of the Internatinal Searching Authority (3 pages), International Search Report (6 pages), and Written Opinion of the International Searching Authority (9 pages) in International Application PCT/GB2008/003260, dated Apr. 23, 2009.

McElfresh, P. et al.: "A Study of the Friction Pressure and Proppant Transport Behavior of Surfactant-Based Gels," SPE77603, Sep. 29, 2002, XP007908186 (14 pages).

\* cited by examiner

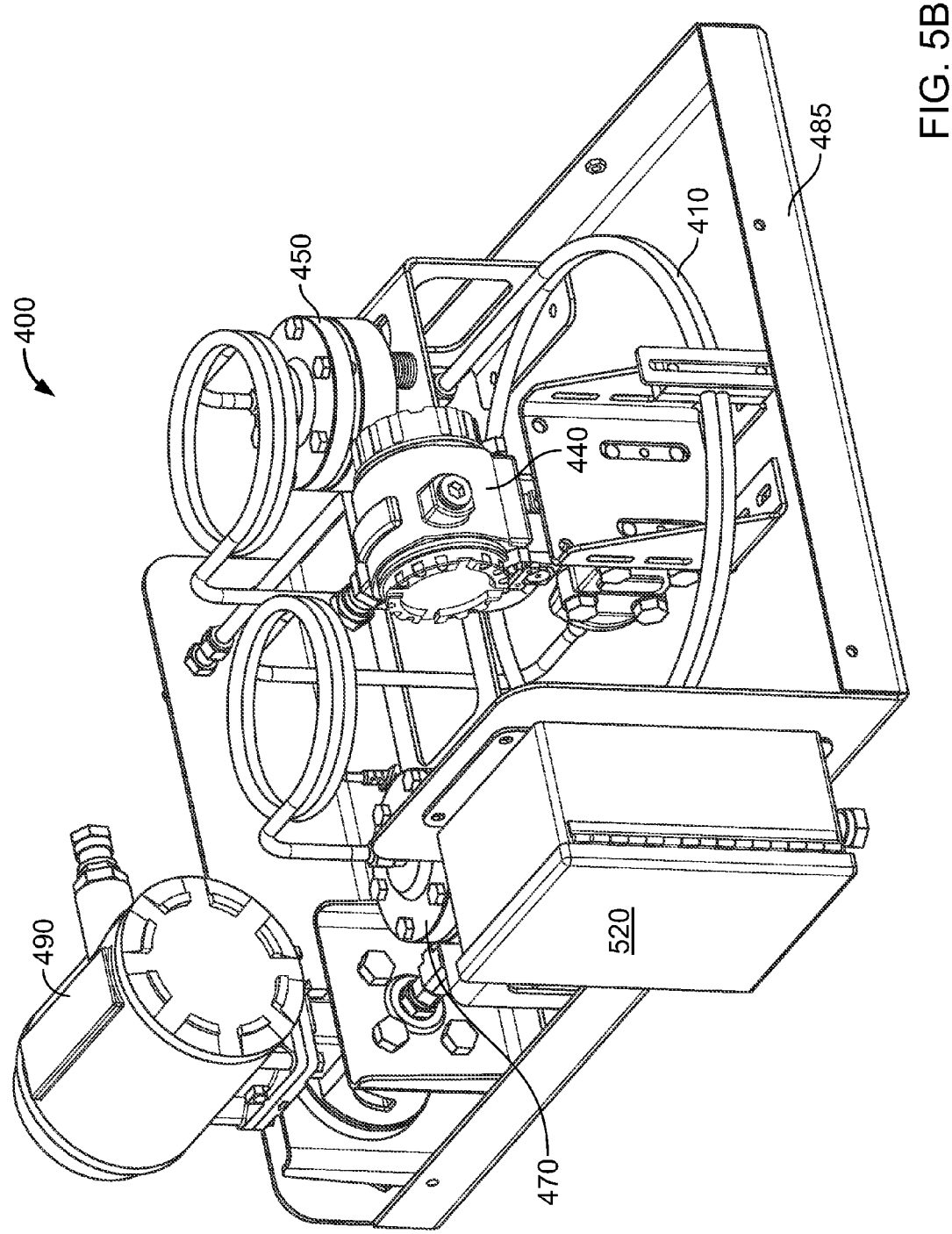

DETERMINING FLUID RHEOLOGICAL PROPERTIES

CROSS REFERENCE TO RELATED APPLICATION

This application is a divisional and claims the benefit under 35 U.S.C. §120 of U.S. patent application Ser. No. 11/868,399, entitled "Determining Fluid Rheological Properties," filed Oct. 5, 2007, which is incorporated herein by reference in its entirety.

TECHNICAL FIELD

This disclosure relates to determining fluid rheological properties.

BACKGROUND

In oilfield applications, there are many instances where it is desirable to know the viscosity or rheological properties of a fluid. For example, a fracturing operation involves pumping a fracturing fluid into a subterranean zone in order to create fractures in the rock of the subterranean zone. The fractures provide flow passages that convey fluids between the subterranean zone and the wellbore. The distance that the fractures penetrate into the subterranean zone (i.e., fracture length) is a function of, among other things, the pressure that can be generated within or near the subterranean zone. Furthermore, this fracture length is a also a function of flow rate into the subterranean zone. To optimize pressure and flow rate at the subterranean zone, the fracturing fluid is typically injected rapidly into or near the subterranean zone. Rapid injection has large associated costs, though, such as the amount of pumping power required to quickly inject the fracturing fluid. The pumping power may be reduced and the fracturing fluid may be introduced more quickly by altering (e.g., lowering) the frictional drag characteristics of the fluid, such as with friction reducing additives. The amount of some friction reducing additives must be carefully controlled to maintain the friction reduction of the fracturing fluid at a desired level. The width of the created fracture is function of the fluid viscosity of the fracturing fluid at the subterranean zone. Gelling agents used to generate viscosity have costs and other undesirable effects. The fluid viscosity must be carefully controlled to maintain the viscosity at a desired level to optimize desired effects (e.g., fracture width) while minimizing undesired effects (e.g., cost).

SUMMARY

The present disclosure relates to determining fluid rheological properties for improving a fracturing operation. One aspect encompasses a method for controlling a well injection operation. According to the method, a flow characteristic of a fracturing fluid is identified, and a flow characteristic of a base fluid used for forming the fracturing fluid is identified. The method also encompasses determining an amount of friction reduction change of the fracturing fluid in relation to the flow characteristic of the fracturing fluid and the flow characteristic of the base fluid and adjusting the amount of friction reduction of the fracturing fluid to coincide with a selected friction reduction amount.

Another aspect encompasses a rheology measuring device. The rheology measuring device includes a measurement tube, a first pressure sensor is disposed at a first position on the measurement tube, and a second pressure sensor disposed at a second position on the measurement tube. A flow meter is disposed at a third position along the measurement tube. The rheology measuring device also includes a temperature sensor disposed at a fourth location along the measurement tube and a control unit interconnected to the first and second pressure sensors, the flow meter, and the temperature sensor.

Another aspect encompasses a method for measuring a rheological property of a fluid. The method encompasses passing a fluid flow through a measurement tube at a selected flow characteristic. The pressure of the fluid flow is determined at a first location along the measurement tube. Additionally, a pressure of the fluid flow is determined at a second location along the measurement tube. A pressure difference of the fluid flow is determined between the first and second locations, and a viscosity of the fluid is determined based on the pressure difference.

The various aspects can include one or more of the following features. Identifying the flow characteristic of the fracturing fluid can include measuring a pressure change of a flow of the fracturing fluid at a selected flow rate. Measuring the pressure change of the flow of the fracturing fluid at the selected flow rate can include measuring the pressure change of the flow of the fracturing fluid at a flow rate corresponding to a flow rate at which the fracturing fluid is being injected into the well. Identifying the flow characteristic of the fracturing fluid can include measuring a pressure change of a flow of the fracturing fluid at one of a selected shear rate, Reynolds Number, fluid velocity, flow rate, flow noise, or other descriptor that characterizes the flow. Identifying the flow characteristic of the base fluid can include measuring a pressure change of a flow of the base fluid at one of a selected shear rate, Reynolds Number, fluid velocity, flow rate, flow noise, or other descriptor that characterizes the flow, and measuring the pressure change of the flow of the base fluid at the selected flow rate can include measuring the pressure change of the flow of the base fluid at a flow rate corresponding to a flow rate at which the fracturing fluid is being injected into the well. Identifying the flow characteristic of the base fluid used for forming the fracturing fluid can include referencing a compilation of flow property data of the base fluid. Additionally, referencing a compilation of the flow property data of the base fluid can include selecting from a plurality of predetermined flow characteristic data a flow characteristic value of the base fluid corresponding to a flow rate at which the fracturing fluid is being injected into the well. Referencing a compilation of the flow property data of the base fluid can include selecting from a plurality of predetermined flow characteristic data a flow characteristic value of the base fluid at one of a selected shear rate, Reynolds Number, flow velocity, flow rate, flow noise, or other descriptor that characterizes the flow.

The various aspects can also include one or more of the following features. Determining the amount of friction reduction change of the fracturing fluid can include comparing a friction indicator of the base fluid to a friction indicator of the fracturing fluid. Comparing the friction indicator of the base fluid to the friction indicator of the fracturing fluid can include comparing a predetermined pressure change of a flow of the base fluid at one of a selected shear rate, Reynolds Number, fluid velocity, flow rate, flow noise or other descriptor that characterizes the flow to a pressure change of a flow of the fracturing fluid at a corresponding one of a selected shear rate, Reynolds Number, fluid velocity, flow rate, flow noise, or other descriptor that characterizes the flow. Comparing the friction indicator of the base fluid to the friction indicator of the fracturing fluid may include comparing a pressure change of a flow of the base fluid at one of a selected shear rate, Reynolds Number, fluid velocity, flow rate, flow noise or other descriptor that characterizes the flow to a corresponding one of a selected shear rate, Reynolds Number, fluid velocity, flow rate, flow noise, or other descriptor that characterizes the flow.

Further, the various aspects can include one or more of the following features. A portion of the measurement tube may be curved, and the curved portion of the measurement tube may include 1.5 loops. The rheology measurement device may also include an inlet tube and an outlet tube, wherein internal diameters of the inlet tube, the outlet tube, and the measurement tube are the same. A length of the inlet tube may correspond to a length for establishing a laminar flow of a fluid flowing therein at the first position and wherein a length of the outlet tube corresponds to a length for establishing a laminar flow of a fluid flowing therein at the second position. A curved portion of the measurement tube can include 1.5 loops. The first and second pressure sensors can include a pressure transducer operable to measure a pressure difference of a fluid flowing through the measurement tube. The control unit can determine a rheological property of a fluid flowing through the measurement tube. The rheology measurement device can also include a pump operable to pump a fluid through the measurement tube. The control unit can be coupled to the first and second pressure sensors, the flow meter, the temperature sensor, and the pump. The control unit can determine a fluid flow rate through the measurement tube via the flow meter and control the pump to establish a flow rate of the fluid through the measurement tube at a selected flow rate. The flow meter can be one of an electromagnetic flow meter, a coriolis flow meter, an ultrasonic flow meter, a vortex flow meter, a turbine flow meter, or positive displacement flow meter. Additionally, the various aspects can control a flow rate of the fluid flow through the measurement tube to maintain the selected control characteristic, and the selected flow characteristic can be a shear rate.

The details of one or more implementations are set forth in the accompanying drawings and the description below. Other features, objects, and advantages will be apparent from the description and drawings, and from the claims.

DESCRIPTION OF DRAWINGS

FIGS. 5A and 5B illustrate different views of an example rheology measuring device;

DETAILED DESCRIPTION

Figure 1:
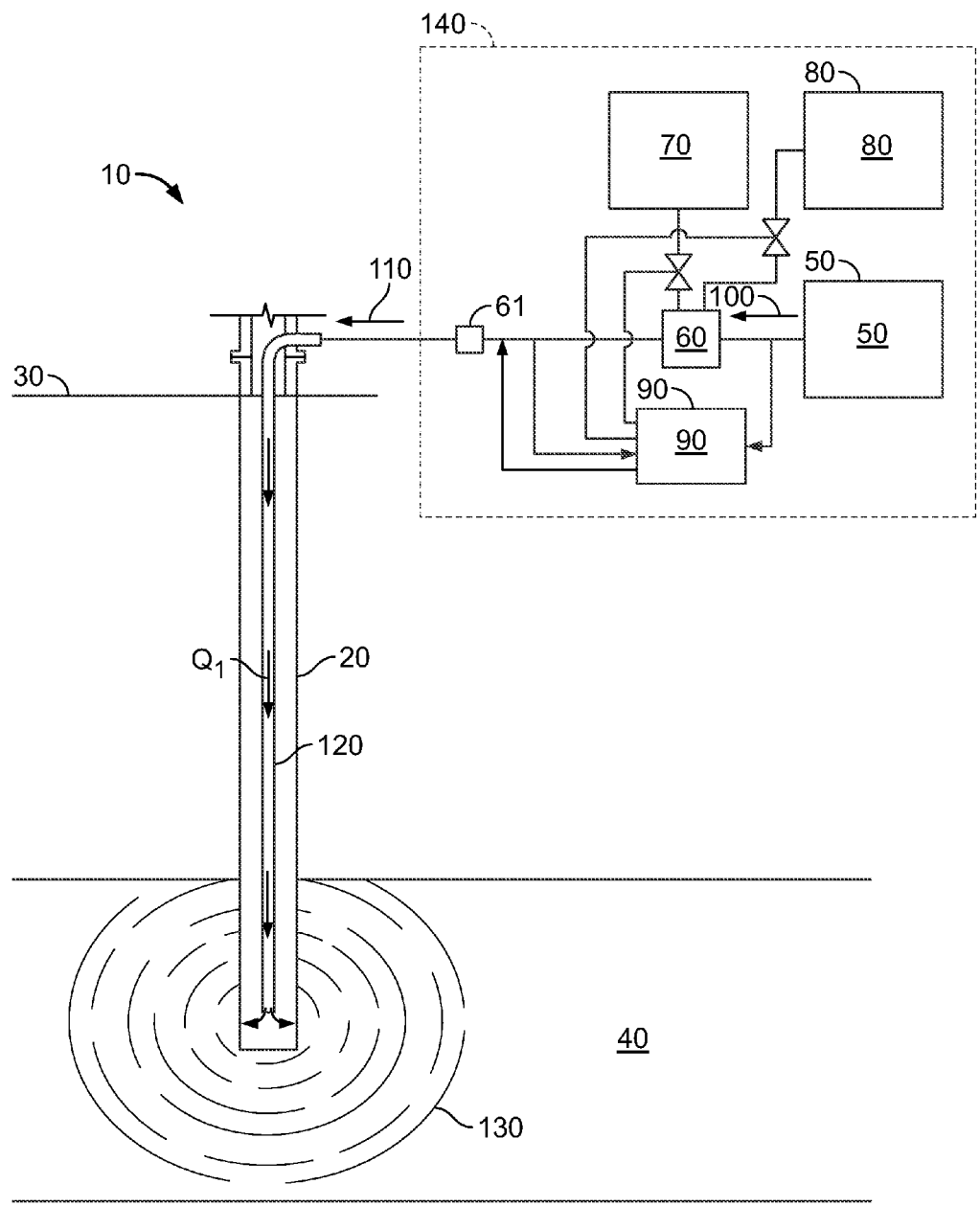
FIG. 1 is an example system for monitoring and controlling a composition of a fracturing fluid.

FIG. 1 shows an example system 10 for monitoring and controlling properties of a fracturing fluid used in a fracturing operation. As shown, the fracturing fluid is injected into a wellbore 20 formed below a surface 30. The wellbore 20 extends to a subterranean zone 40. Although the wellbore 20 is shown as penetrating the subterranean zone 40, the wellbore 20 may extend through or terminate near the subterranean zone 40. The system 10 also includes one or more storage tanks 50 containing a base fluid. The base fluid may be formed from a combination of water and a gel polymer. The base fluid may be used to form the fracturing fluid. The system 10 further includes a blender apparatus 60 for blending the base fluid and a friction reducer 70 and other optional additives, such as a proppant 80. The system may also include a measurement and control module 90 for monitoring a condition of the base fluid and a condition of the fracturing fluid.

At a high level, the base fluid 100 enters the blender apparatus 60 where it is combined with an amount of the friction reducer 70 and/or proppant 80. Once combined, the resulting fracturing fluid 110, exits the blender apparatus 60 and is pumped, via a pump 61, through a tubing string 120 for injection into the wellbore 20, for example. The fracturing fluid 110 exits the tubing string 120 in or near the subterranean zone 40 where the fracturing fluid 110, under pressure, enters and produces fractures (interchangeably referred to as a fracture network) 130 in the rock of the subterranean zone. A blending portion 140 of the system 10 is described in more detail below.

Figure 2:
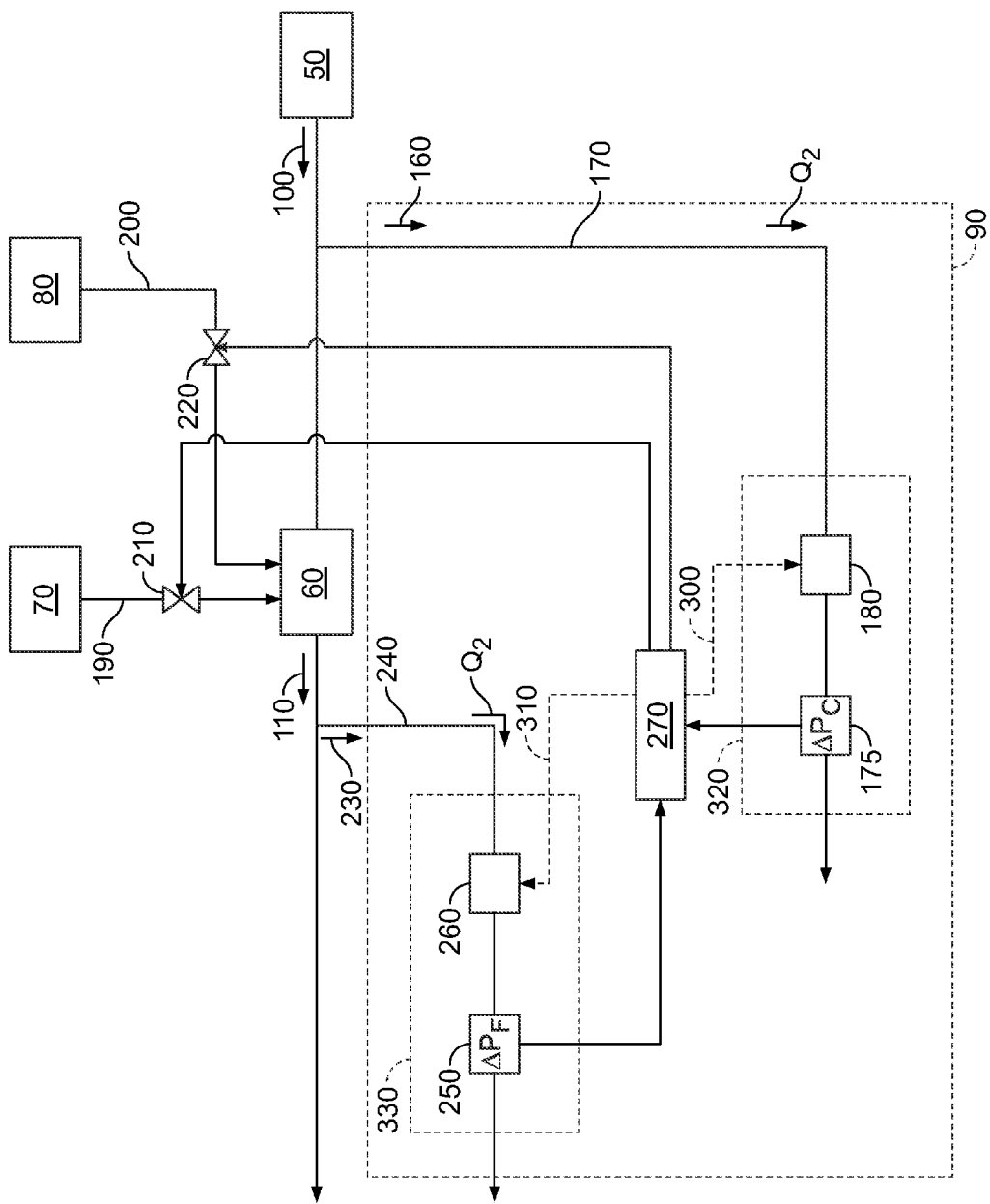
FIG. 2 is a detail view of a portion of the system of FIG. 1.

FIG. 2 shows the blending portion 140 of the system 10 according to one implementation. As explained above, the base fluid 100 is delivered to the blender apparatus 60 from the storage tank 50. A portion 160 of the base fluid 100 is diverted via a conduit 170, and a pressure change, $\Delta P_C$, (i.e., a fluid pressure change along a specified flow distance) of the portion 160 is measured by a first pressure measurement instrument 175. Some examples of the first pressure measurement instrument 175 include the Rosemount 3051 series differential pressure transducers, the Endress+Hauser PMD7X series and FMD7X series differential pressure transducers, as well as other devices for measuring pressure. The first pressure measurement instrument 175 may include two independent, non-differential pressure transducers provided on the conduit 170 coupled to a processing unit. The processing unit may be operable to determine a pressure difference from a pressure measurement of each of the transducers and output the pressure difference. Additional examples of the first pressure measurement instrument 175 include the Rosemount 3051 series non-differential pressure transducers and the Endress+Hauser PMP7X series and PMC7X series non-differential pressure transducers. A first flow control device 180 is also disposed along the conduit 170 for controlling a flow rate of the portion 160 at a selected level. As used herein, flow rate may include volumetric or mass flow rate. Some examples of flow control device 180 include a pump, a control valve, or other devices for controlling flow. An example pump may be a positive displacement metering pump. The remainder of the base fluid 100 enters the blender apparatus 60 and is combined with an amount of friction reducer 70 and/or proppant 80. The friction reducer 70 is conveyed to the blender apparatus 60 via a conduit 190, and the proppant 80 is conveyed to the blender apparatus 60 via a conduit 200. According to some implementations, the friction reducer 70 is operable to reduce the pressure loss of the fracturing fluid 110 over a range of concentration of the friction reducer 70. Examples of friction reducers 70 include, but are not limited to, anionic and cationic polyacrylamide polymers, guar, hydroxypropyl guar (HPG), carboxymethyl hydroxypropyl guar, hydroxyethylcellulose, and Xanthan. The friction reduction characteristics of an example friction reducer are discussed in more detail below with reference to FIG. 3. Additive control devices 210 and 220 are disposed along the conduits 190 and 200, respectively, for controlling a flow of the friction reducer and proppant. Some examples of additive control devices include a flow control valve, measuring screw, or other device. Although not illustrated, other additives can be added into the blender apparatus 60 for incorporation with the base fluid. Some examples of other additives can include borate, titanate, and zirconate cross linking agents, biocides, pH control agents such as formic acid or caustic soda, enzymatic and oxidizing breakers, clay stabilizers or other additives. The other additives may be added in lieu of or in combination with the friction reducer 70 and/or proppant 80. Although FIG. 2 illustrates one example location of conduit 170, the conduit 170 may be provided at other locations to draw off a portion of the base fluid 100. That is, conduit 170 may be located to draw off a portion of the base fluid 100 prior to the addition of, for example, the proppant 80, the friction reducer 70, or other additives that may be subsequently added to the base fluid.

The fracturing fluid 110 exits the blender apparatus 60. A portion 230 of the fracturing fluid 110 is diverted into a conduit 240 and is measured by a second pressure measurement instrument 250. Some examples of pressure measurement instrument 250 include a Rosemount 3051 series differential pressure transducer, a Endress+Hauser PMD7X series and FMD7X series differential pressure transducer, as well as other devices for measuring pressure. The second pressure measurement instrument 250 may also include two independent, non-differential pressure transducers provided on conduit 240 coupled to a processing unit. The processing unit may be operable to determine a pressure difference from a pressure measurement of each of the transducers and output the pressure difference. Additional examples of the first pressure measurement instrument 250 include the Rosemount 3051 series non-differential pressure transducers and the Endress+Hauser PMP7X series and PMC7X series non-differential pressure transducers. The second pressure measurement instrument 250 measures a pressure change, $\Delta P_F$, e.g., a fluid pressure change along a specified flow distance, of the portion 230. The conduit 240 also includes a second flow control device 260, for controlling a flow rate of the portion 230 at a selected level. Some examples of the flow control device 260 include a pump, a control valve, or other devices for controlling flow. An example pump used as the flow control device 260 may include a positive displacement metering pump. The remainder of the fracturing fluid 110 is conveyed to the wellbore 20 and injected into or near the subterranean zone 40 to form fractures 130.

The measured pressure changes, $\Delta P_F$ and $\Delta P_C$, of the portions 160 and 230 are transmitted to a control unit 270. The control unit 270 determines a friction reduction value which corresponds to a friction reduction ratio ("FRR") of $\Delta P_F$ to $\Delta P_C$ or vice versa. The FRR provides a comparison of the friction pressure drop of the base fluid 100 without additives added at blender apparatus 60 and the fracturing fluid 110. Consequently, this ratio may be used to determine an amount of friction reduction of the fracturing fluid 110 has been achieved. Once the ratio is determined, the ratio is compared to a selected target ratio. According to some implementations, the target FRR is selected to provide the greatest amount of friction reduction of the fracturing fluid relative to the base fluid that can be achieved with the particular friction reducer additive.

The addition of a friction reducer to a liquid, such as the base fluid 100, may result in fluid friction reduction over a concentration range of fluid reducer. However, the viscosity of the fluid may appear to increase as the fluid friction decreases. The apparent discrepancy may be the result of the flow profile established when fluid measurements are taken, for example, a laminar flow profile versus a turbulent flow profile. For example, measurement of a fluid having a dynamic viscosity of 3 cP at a flow rate of 511 sec$^{-1}$, for example, corresponds to a Reynolds Number ($N_{re}$) of approximately 1000, which indicates a laminar flow regime. At the same flow rate, the flow regime would remain laminar as the viscosity increases. However, when a fluid used in a fracturing operation is measured under the same or approximately the same conditions that exist during the fracturing operation, e.g., the same flow rate that the fluid is flowing through the well tubulars, a measured friction pressure of the fluid is reduced. For example, an example fracturing operation may involve flowing a fracturing fluid through a 2.441 inch diameter well tubular at a rate of 20 bbl/min. The fracturing fluid may have a dynamic viscosity of 24 cP (when measured at 511 sec$^{-1}$ and having a Reynolds Number of 127 (laminar)). When measured under the above fracturing conditions, the fracturing fluid may have a Reynolds Number of approximately 100,000, which is a highly turbulent flow. The friction reducer added to the fracturing fluid may include long-chain polymers. At this flow rate, the friction reduction caused by the long-chain polymers is noticeable while the friction increase caused by viscous effects are negligible. Thus, a fluid having a high dynamic viscosity when measured under a laminar flow regime may have noticeable friction reduction under fracture operation conditions due to the added friction reducer. At increased concentrations of the friction reducer, the viscous effects may offset the friction reduction causing the fluid's friction reduction ratio increase, as shown in FIG. 3.

Figure 3:
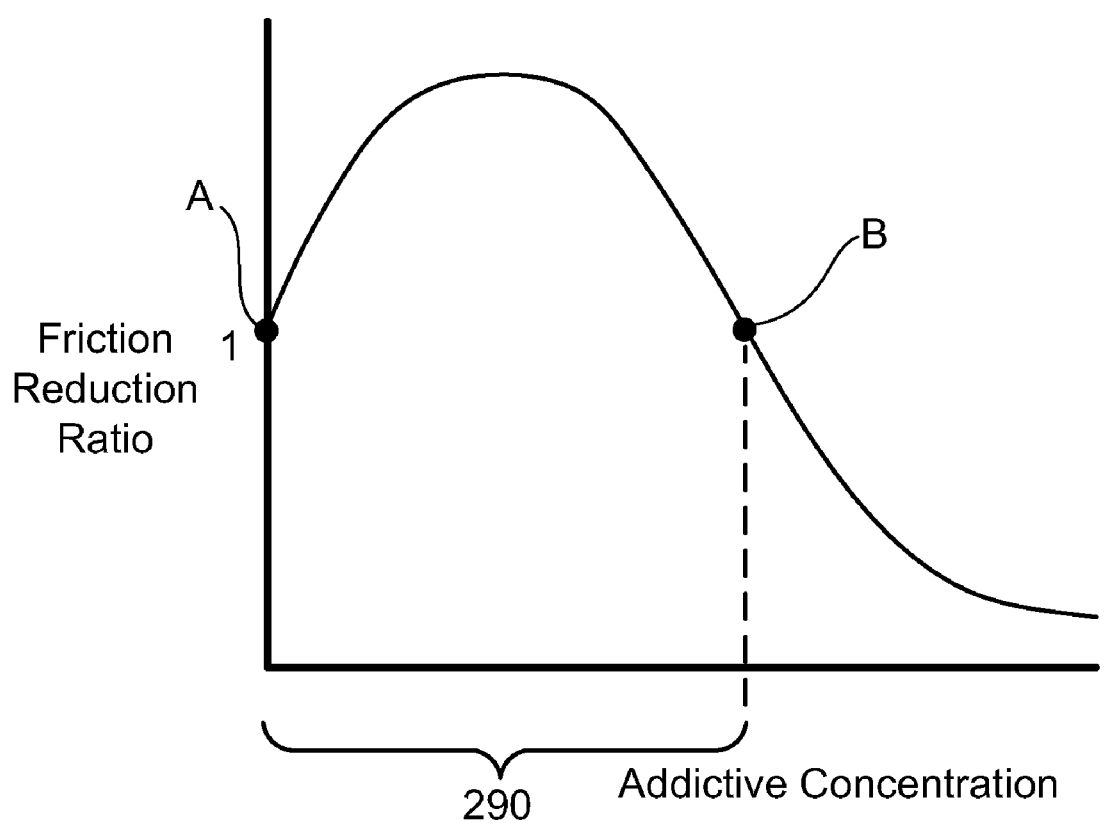
FIG. 3 is a graph indicating friction reduction of a fluid with changing additive concentration.

FIG. 3 is a graph 280 of the friction reduction behavior of an example fracturing fluid as a function of the amount of added example friction reducer. Concentration range 290 (between points A and B) is the concentration of the additive that increases the friction reduction ratio of the fracturing fluid. The concentration range of the additive beyond Point B causes the viscosity of the fracturing fluid to increase. The concentration range of the additive below Point A causes little to no change in the friction of the fracturing fluid. Thus, during a fracturing operation, a frictional pressure drop of the fracturing fluid can be decreased if the additive concentration is maintained within the range 290. As a result, the amount of power required to pump the fluid may be reduced.

Referring again to FIG. 2, the selected target ratio may be selected so as to correspond to a fracturing fluid having a concentration of one or more additives resulting in the lowest possible frictional pressure drop as illustrated, for example, in FIG. 3, described above. The selected target FRR is determined based on different considerations which may or may not be unique to a particular fracture operation, such as one or more of the chemical composition of the base fluid, the additive being used, the amount of other additives added to the fracturing fluid, the equipment being used to perform the fracturing operation, the nature of the subterranean zone, the strata adjacent to or otherwise proximate to the subterranean zone, or other considerations. Once the measured FRR is compared with the selected target FRR, the control unit 270 determines whether any changes to the amount of one or more additives should be made in order to maintain the fracturing fluid at a desired FRR. To effect a change the control unit 270 may transmit a signal to one or more of the additive control devices 210 or 220 to adjust addition of the respective additives. Although not shown, the control unit 270 may also transmit signals to other control devices that control the addition of other additives that may be added to the fracturing fluid.

If the fracturing fluid behaves as a non-Newtonian fluid, such as because of the addition of some additives, the viscosity of the fracturing fluid is shear rate dependent. That is, the viscosity of the fracturing fluid changes depending upon the fracturing fluid's shear rate. The shear rate may change depending upon, for example, the geometry of the pipe, e.g., inner pipe diameter, through which a fluid flows, the path of the flow, the velocity of the fluid, etc.

Thus, according to one implementation, the flow characteristics of the fracturing fluid down the wellbore 20 (e.g., tubing string 120) and/or in or near the subterranean zone 40 are identified. The flow, $Q_1$ (shown in FIG. 1), of the fracturing fluid within the tubing string 120 and/or in or near the subterranean zone 40 can be determined, for example by estimating or by measurement. The flow, $Q_2$, of the fracturing fluid within the conduit 240 can be made to correspond. That is, the flow rate $Q_2$ may be made to model the flow of the $Q_1$. For example, the flow $Q_1$ of the fracturing fluid through the tubing string 120 may be characterized by determining or approximating a shear rate, Reynolds Number, or other descriptor that characterizes the flow. The flow $Q_2$ within the conduit 240 can be created to correspond to that of $Q_1$ for example by matching or making a corresponding shear rate, Reynolds Number, or other descriptor that characterizes the flow to the flow $Q_1$ within the tubing string 120. Further, in a fracturing operation, the fracturing fluid injected into a wellbore is generally turbulent. Thus, $Q_1$ may be a turbulent flow. Accordingly, the flow $Q_2$ may also be defined to be a turbulent flow. However, according to other implementations, $Q_1$ may be a laminar flow, and, as such, $Q_2$ may be defined as a laminar flow.

Referring again to the implementation shown in FIG. 2, the flow rate of $Q_2$ through the conduit 240 having a shear rate, Reynolds Number, or other descriptor that characterizes the flow corresponding to the flow $Q_1$ through the tubing string 120 may be determined. The modeled flow $Q_2$ through to the conduit 240 may also be applied to the flow of the base fluid through the conduit 170 (also labeled $Q_2$ in FIG. 2). The flows $Q_2$ within the conduits 170 and 240 may be maintained by the flow control devices 180 and 260, respectively. For example, the flow control devices 180 and 260 may include a flow meter for measuring the flow rate and a pump or throttling valve for adjusting the flow rates to match a target flow rate corresponding to the modeled flow. According to some implementations, the flow control devices 180 and 260 may be self contained, i.e., the measurement and adjustment of the flows through the conduits 170 and 240 are entirely controlled by the flow control devices 180 and 260. According to other implementations, the flow rate measurements from the flow control devices 180 and 260 may be transmitted to the control unit 270 and control signals 300 and 310 may be transmitted to the flow control devices 180 and 260 to adjust the fluid flows. As explained above, maintaining the flows $Q_2$ includes maintaining the flows $Q_2$ at a turbulent flow rate, although the flows $Q_2$ may be maintained at other flow rates, such as a laminar flow rate. Consequently, the flows $Q_2$ may be maintained at either a turbulent flow condition, laminar flow condition, or other desired flow condition.

Once the flow $Q_2$ is established in the conduits 170 and 240, the $\Delta P_F$ and $\Delta P_C$ may be measured, and a FRR may be determined. The control unit 270 compares the target FRR and the measured FRR and adjusts the amount of additives to the base fluid to provide the fracturing fluid with the desired friction reduction.

According to another implementation, the FRR is determined at a selected shear rate, Reynolds Number, or other descriptor that characterizes the flow of both the base fluid 100 and the fracturing fluid 110. That is, the FRR is determined by measuring $\Delta P_F$ and $\Delta P_C$ at a common flow descriptor value. For example, a shear rate of 10,000 $sec^{-1}$ or a Reynolds Number of 100,000. By determining the FRR at a selected flow descriptor, the tubing string geometry, such as the inner diameter of the tubing, need not be known. Accordingly, the flows of portions 160 and 230 through the conduits 170 and 240, respectively, are adjusted until the flows possess the selected flow descriptor. For example, the fluid properties of the base fluid 100 and the fracturing fluid 110 may be known, including the flow descriptor value of the fluids at a given flow rate and may be provided in one or more sets of data. For the fracturing fluid 110, numerous sets of data may be included for fracturing fluids having different compositions. Depending upon the amount and type(s) of additive(s) being applied one or more times during the fracturing operation, the appropriate data set may be referenced and, thus, the appropriate data may be utilized. Because the composition of the fracturing fluid 110 may change during the fracturing operation, the data set being used may change.

Consequently, the flow rates, $Q_2$, of portions 160 and 230 may be adjusted to correspond with a flow rate having the desired flow descriptor value. The flow rates of the portions 160 and 230 may be adjusted manually or automatically via the flow control devices 180 and 260. For automatic control, the control unit 270 may include the data sets for the fracturing fluid 110 and the base fluid 100 listing flow rates with the corresponding shear rates. The control unit 270 may then adjust the flows of portions 160 and 230 to a flow rate having the desired flow descriptor values using the flow control devices 180 and 260.

When the flows of portions 160 and 230 have been adjusted to a desired flow rate, the $\Delta P_F$ and $\Delta P_C$ may be measured and the FRR determined. Thereafter, the control unit 270 may transmit signals to the additive control devices 210 and 220 to achieve the target FRR. Once the portions 160 and 230 have been measured, the fluids may be returned to the base and fracturing fluids 100 and 110, respectively, or otherwise discharged from the system 10.

According to another implementation, the conduit 170, the first pressure measurement instrument 175, and the flow control device 180 may be eliminated and replaced with measured or simulated data for the base fluid 100. For example, the base fluid 100 may remain relatively unchanged during the fracturing operation. Consequently, the composition and properties of the base fluid 100 remain relatively constant. As such, the properties of the base fluid 100 may be determined by testing and/or simulation performed prior to the fracturing operation. Once the properties of the base fluid 100, such as the $\Delta P_C$ and viscosity of the base fluid at different shear rates and velocities are determined, the information (referred to hereinafter as "fluid property information") may be recorded and stored for subsequent use. Therefore, at a fracturing operation, the stored fluid property information of the base fluid 100 may be manually or automatically applied to determine the FRR. The fluid property information of the base fluid 100 may be stored and/or applied by the control system 270 to adjust the addition of the additives for maintaining the viscosity of the fracturing fluid 110 at a desired level.

A further implementation combines features of the above implementations in that the conduit 170, the first pressure measurement instrument 175, and the flow control device 180 may be eliminated and replaced with measured and/or simulated data fluid property information for the base fluid 100, and the FRR may be determined at a selected flow descriptor value, thus eliminating the need to know the flow characteristics of the fracturing fluid 110 through the tubing string 120. As such, the flow rate of portion 230 may be controlled, such as with the flow control device 260, to correspond to a selected flow descriptor value. Further, stored data of the base fluid may be referenced to identify the $\Delta P_C$ corresponding to the selected flow descriptor value.

As a result, the flow rate of the portion 230 through conduit 240 may be adjusted to correspond to the selected flow descriptor value. The resulting $\Delta P_F$ may then be determined. Also, the $\Delta P_C$ may be identified by referencing the fluid property information for the base fluid. Thus, the FRR may be determined and the amount of additives adjusted, if needed, to achieve the selected friction reduction of the fracturing fluid 110.

The first pressure measurement instrument 175 and the first flow control device 180 may form a portion of a rheology measurement device ("RMD") 320, and the second pressure measurement instrument 250 and the second flow control device 260 may form a portion of an RMD 330. According to other implementations, one or more of the RMDs 320 the 330 may be disposed in the system 10 to directly measure one or more of the base fluid 100 and the fracturing fluid 110.

The RMDs 320 and 330 may be substantially similar. According to some implementations, an RMD 400, illustrated in FIGS. 4, 5A, and 5B, may be used as the RMDs 320 and 330. For simplicity purposes, the RMD 400 shown in FIGS. 4, 5A, and 5B will be used throughout the remainder of the disclosure for explaining the construction and operation of the RMD, according to some implementations, although it will be understood that the description of RMD 400 may also apply to RMD 320 and 330.

Figure 4:
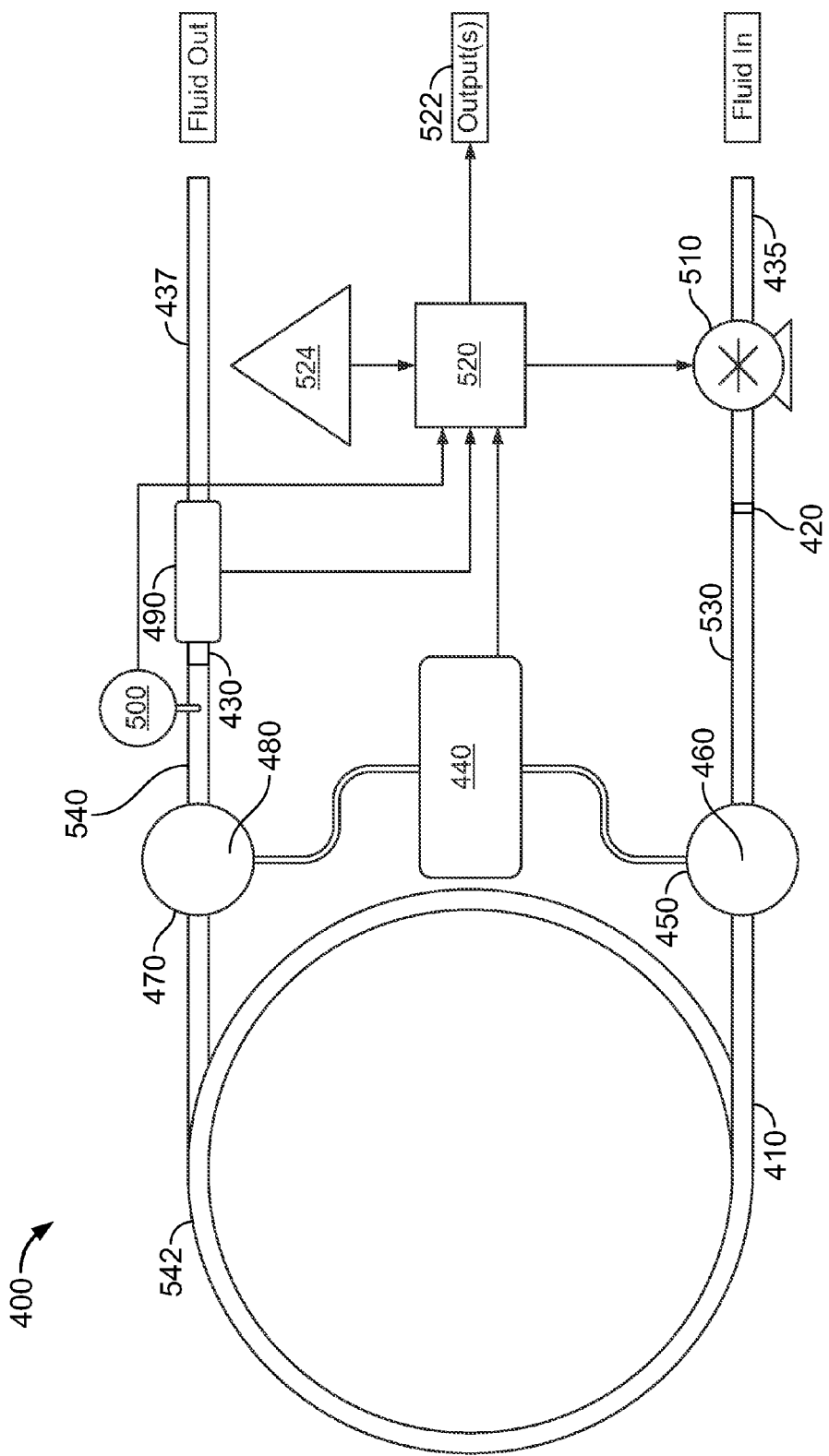
FIG. 4 is a schematic view of an example rheology measuring device.
Figure 5A:
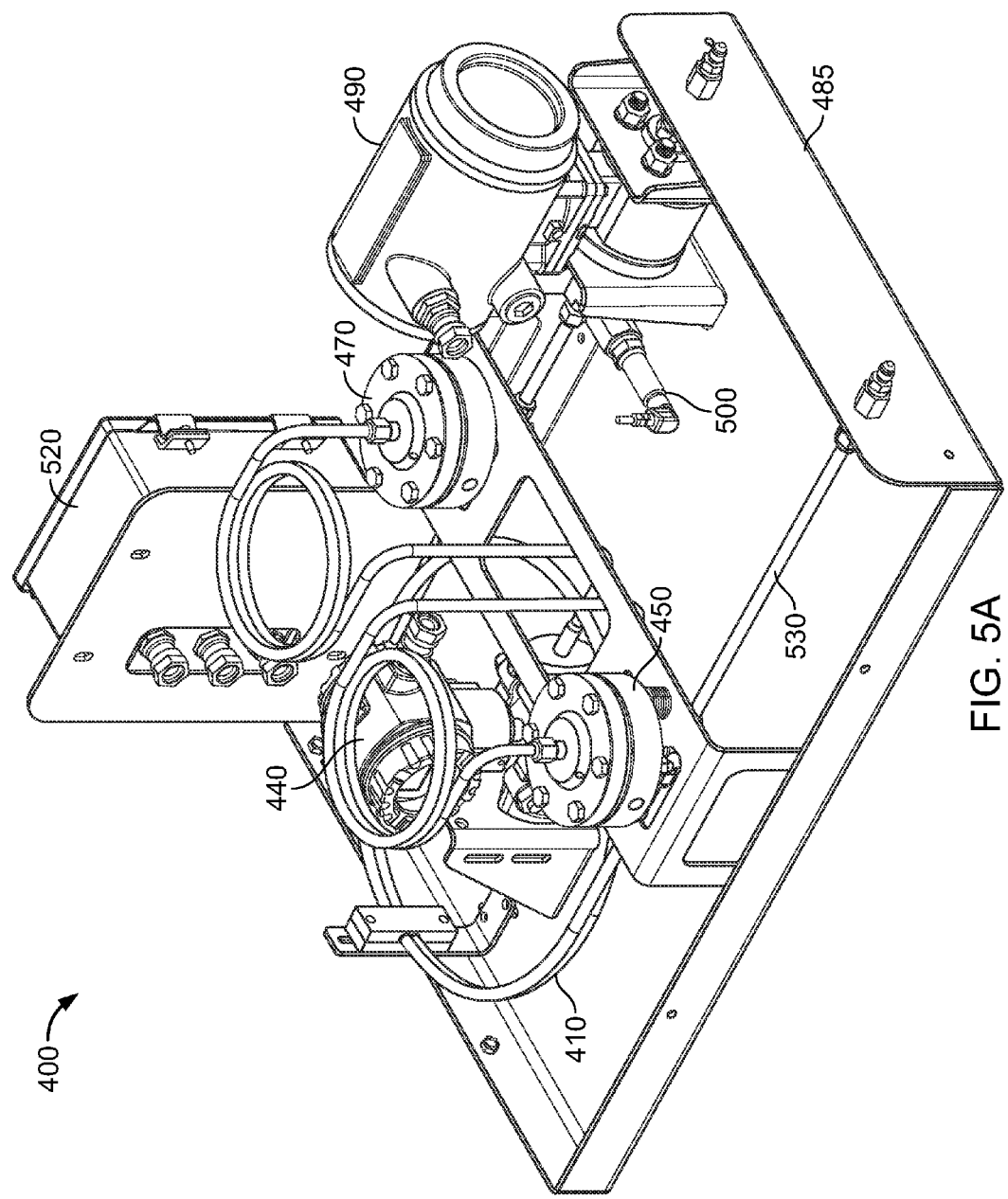
Figure 6:
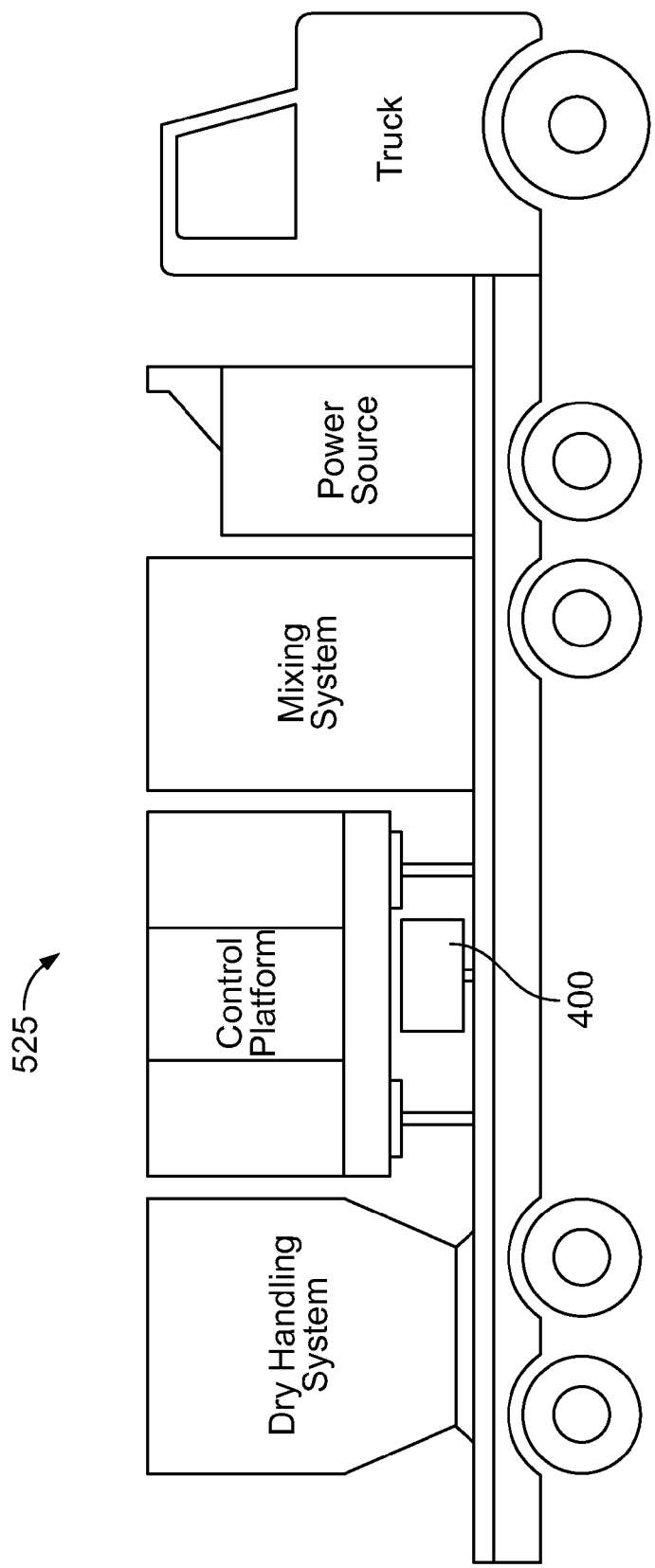
FIG. 6 shows an example mobile fracturing apparatus incorporating the rheology measuring device.

A schematic view of the RMD 400 is shown in FIG. 4. The RMD 400 includes a measurement tube 410, having an inlet 420 and an outlet 430; an inlet tube 435; and outlet tube 437; a differential pressure sensor 440 having a first pressure sensor 450 disposed at a first location 460 of the measurement tube 410 and a second pressure sensor 470 disposed at a second location 480 of the measurement tube 410; a flow meter 490, and a temperature sensor 500. According to some implementations, the flow meter 490 may be a coriolis flow meter, electromagnetic flow meter (interchangeably referred to as "magnetic flow meter"), vortex flow meter, turbine flow meter, or positive displacement flow meter. According to some implementations, a coriolis flow meter may be a straight or bent tube coriolis flow meter. Additionally, a flow meter or other instrumentation that determines fluid flow properties based on a flow noise or noise signal generated by the fluid may also be used. For example, such instrumentation may include a flow meter, a microphone, or pressure transducer optimized to detect a noise signal corresponding to turbulence of the fluid flow. Example flow meters may include an electromagnetic flow meter or an ultrasonic flow meter. Such flow meters may provide a bulk flow rate as well as additional information regarding higher frequency variations in flow rate caused by turbulence. The RMD 400 may also include a pump 510 that may be utilized to adjust a flow of the fluid being measured passing through the measurement tube 410. The pump 510 may be disposed in or attached to the inlet pipe. For example, the pump may be driven by a motor 515, such as a 24 volt DC motor, a 110 volt AC motor, a hydraulic motor, a pneumatic motor, or other known drive mechanisms. Additionally, the RMD 400 also includes a control unit 520 for monitoring, collecting data, and/or controlling one or more operations of the RMD 400. The components of the RMD 400 may be sized or arranged to occupy a small volume for convenient transportation and may be attached directly or indirectly to a chassis 485 (shown in FIGS. 5A and 5B). For example, the RMD 400 may be incorporated into a mobile fracturing apparatus 525, such as the mobile fracturing vehicle shown in FIG. 6. As shown, the RMD 400 is disposed on the mobile fracturing apparatus 525, such as below the control platform.

The control unit 520 may be implemented in digital electronic circuitry, or in computer software, firmware, or hardware, including the structural means disclosed in this specification and structural equivalents thereof, or in combinations of them. The control unit 520 can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The control unit 520 may include one or more processors that execute instructions and manipulates data to perform the operations and may be, for example, a central processing unit (CPU), a blade, an application specific integrated circuit (ASIC), or a field-programmable gate array (FPGA). Processors suitable for the execution of a computer program include, by way of example, both general and special purpose microprocessors, and any one or more processors of any kind of digital computer. Generally, the processor will receive instructions and data from ROM or RAM or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The control unit 520 may also include one or more memory devices. Each memory device may include any memory or database module and may take the form of volatile or non-volatile memory including, without limitation, magnetic media, optical media, random access memory (RAM), read-only memory (ROM), removable media, or any other suitable local or remote memory component. The one or more memory devices may include application data for one or more applications, as well as data involving VPN applications or services, firewall policies, a security or access log, print or other reporting files, HTML files or templates, related or unrelated software applications or sub-systems, and others. Consequently, the memory may also be considered a repository of data, such as a local data repository for one or more applications.

The control unit 520 may also include an output device, such as a display device, e.g., a cathode ray tube ("CRT") or LCD (liquid crystal display) monitor, for displaying information to the user as well as an input device, such as a keyboard and a pointing device, e.g., a mouse or a trackball, by which the user can provide input to the computer. Other kinds of devices can be used to provide for interaction with a user as well to provide the user with feedback. For example, feedback provided to the user can be any form of sensory feedback, e.g., visual feedback, auditory feedback, or tactile feedback; and input from the user can be received in any form, including acoustic, speech, or tactile input.

The application may be any application, program, module, process, or other software that may utilize, change, delete, generate, or is otherwise associated with the data and/or information associated with one or more control operations of the RMD 400. "Software" may include software, firmware, wired or programmed hardware, or any combination thereof as appropriate. Indeed, the application may be written or described in any appropriate computer language including C, C++, Java, Visual Basic, assembler, Perl, any suitable version of 4GL, as well as others. It will be understood that, while the application may include numerous sub-modules, the application may instead be a single multi-tasked module that implements the various features and functionality through various objects, methods, or other processes. Further, while the application may be internal to control unit 520, one or more processes associated with the application may be stored, referenced, or executed remotely (e.g., via a wired or wireless connection). For example, a portion of the application may be a web service that is remotely called, while another portion of the application may be an interface object bundled for processing at remote client. Moreover, the application may be a child or sub-module of another software module or application. Indeed, the application may be a hosted solution that allows multiple parties in different portions of the process to perform the respective processing.

At a high level, the RMD 400 uses a closed-loop flow control to adjust a flow of the fluid passing through the measurement tube 410. The pump 510 may be used to maintain the flow at a selected level. A pressure differential, $\Delta P$, of the fluid is measured between the first and second locations 460 and 480. The $\Delta P$ and flow rate are used by the control unit 520 to determine a viscosity of the fluid or other rheological properties, such as pressure drop versus flow rate, pressure drop versus shear rate, pressure drop versus a measure of turbulence (e.g., Reynolds Number), and the fluid-specific descriptive coefficients in fluid models, such as the Power Law model. The temperature of the fluid, measured by the temperature sensor 500, is used to provide information about the fluid when a $\Delta P$ measurement is made. The rheological properties of most fluids change with temperature. Thus, it is common to make standardized measurements referenced to a particular temperature, for example, 25° Celsius. Temperature sensor 500 can be used with an appropriate fluid model to adjust a measurement from the temperature measured to a reference temperature or to another temperature. Thus, the temperature measurement, such as a temperature measurement made by the temperature sensor 500, may be used to compare fluid properties determined at the measured temperature to a standard reference determined at a different temperature or extrapolate the measured properties out to a different temperature. The conversion may be accomplished with an appropriate fluid model. Additionally, viscosity measurements are temperature sensitive, and, in some cases, a one degree Fahrenheit change in temperature can correspond to a two percent variance in the viscosity. Therefore, it is important to measure a fluid's temperature at location close in proximity to where the fluid's properties are measured. Further, the control unit 520 may be operable to output data 522, such as calculated data or measurement data, e.g., viscosity, $\Delta P$, temperature, and flow rate. The control unit 520 may also be operable to accept programming or other inputs, such as a flow rate setpoint 524.

The RMD 400 provides for a stable platform with the capability of repeatable friction reduction measurement or viscosity measurement results. Additionally, according to one implementation, the latency of obtaining a viscosity measurement is approximately five seconds, e.g., the travel time of the fluid between the first location 460 and the second location 480. Further, the RMD 400 is capable of measuring 15 to 20 times more fluid than presently available systems.

RMDs within the scope of the present disclosure may be used to determine viscosity at a laminar flow rate as well as measure friction reduction of a fluid at a turbulent flow rate. Thus, a fluid may be passed through a measurement tube of the RMD at a flow rate corresponding to laminar flow, and optionally controlled to maintain such a flow rate, to measure viscosity. Other desired rheological properties may also be determined. Also, a fluid may be passed through the flow measurement tube of the RMD at a turbulent flow rate, and optionally controlled to maintain such a flow rate, to measure friction reduction. Similarly, other rheological properties may also be determined.

According to one implementation, the measurement tube 410 is formed from 316L stainless steel having an outer diameter of 0.375 inches and an inner diameter of approximately 0.277 inches, and the measurement tube 410 has a length of approximately 72 inches. The measurement tube 410 may also include an entrance length 530, i.e., a length of the measurement tube 410 between the inlet 420 and the first location 460, of approximately 12 inches and an exit length 540, i.e., the length of the measurement tube 410 between the second location 480 and the outlet 430 of approximately 6 inches. The entrance length 530 and exit length 540 may be selected to establish laminar flow, for example, fully developed laminar flow. Further, the entrance length 530 and exit length 540 may have lengths different than those described above for different implementations. A bend geometry 542 of approximately 1.5 loops extends between the first location 460 and the second location 480. The 1.5 loops have a bend diameter of approximately 12.6 inches. As such, the fluid enters and exits a common side of the RMD 400. Moreover, the internal diameters of the measurement tube 410, the inlet tube 435, and the outlet tube 437 may be the same, which may produce less turbulence and provide a more uniform laminar flow passing through the RMD 400. Additionally, the 1.5 loops may smooth the transition between turbulent and laminar flow thus enabling improved determination of fluid viscosity at lower viscosities when using simple calculation methods.

Although one implementation is described above, other implementations are within the scope of the present disclosure. For example, RMDs having different entrance and exit lengths and different bend diameters are also within the scope of the present disclosure. Further, according to some implementations, the measurement tube does not include a bend. That is, according to some implementations, the measurement tube is straight.

According to one implementation, the differential pressure sensor 440 may be a Rosemount model 3051C, produced by Rosemount Inc. of 8200 Market Boulevard, Chanhassen, Minn. 55317, with PI Component fluid isolators. Alternatively, the differential pressure sensor 440 may be an Endress+Hauser model PMD75, produced by Endress+Hauser, Inc. of 2350 Endress Place, Greenwood, Ind. 46143-9772, with ITT Conoflow fluid isolators produced by ITT Conoflow of 5154 Hwy. 78, St. George, S.C. 29477. Also the flow meter 490 may be a Rosemount model 4711 with a model 8712D transmitter or a Rosemount model 8711 with a model 8732C transmitter, both of which are produced by Rosemont, Inc. The temperature sensor 500 may be a Pyromation model R1T185, 100 ohm resistance temperature detector (RTD) produced by Pyromation, Inc. of 5211 Industrial Road, Fort Wayne, Ind. 46825 or an Endress+Hauser model TSM470G produced by Endress+Hauser, Inc.

The pump 510 may be a progressive cavity pump, such as a Netzsch model NM008BY02S1B produced by Netzsch, Inc., of 119 Pickering Way Exton, Pa., 19341; a Seepex model MD 003-12/A6-A7-A7-H0-GA-X (X=0820, 11H0, 163) produced by Seepex, Inc., of 511 Speedway Drive, Enon, Ohio 45323; or a Seepex model MD 003-12/A6-A7-A7-H0-GA-X (X=04XX, 0802, 11H0, 163, 22XX) produced by Seepex, Inc. The pump 510 may be coupled to motor 515, such as Leeson model C4D17NK10C (catalog number 108051), ½ hp, totally enclosed, non-vented, 24 volt DC electric motor produced by Leeson Electric Corporation of 2100 Washington Street, Grafton, Wis. 53024-0241 or a Baldor model CDP 3430-V24 produced by Baldor Electric Company of 5711 R. S. Boreham, Jr. Street, Fort Smith, Ariz. 72901.

The pump 510 may include run-dry protection to prevent damage to the pump 510 should a run-dry condition occur. According to some implementation, the run-dry protection may include a level switch installed in a cross on a suction line (not shown) of the pump 510. If a fluid level is above the level switch, the level switch closes a circuit to the motor controller, and the pump 510 is operable. If a fluid level is below the level switch, the level switch breaks the circuit, stopping the pump 510. Consequently, the pump 510 may be protected from running dry, i.e., without a fluid flow passing through the pump 510. According to one implementation, the level switch may be an Endress+Hauser model FTL-20 vibrating fork produced by Endress+Hauser, Inc.

According to some implementations, the RMD 400 is packaged as a single module or as numerous separate modules. For example, the RMD 400 may include a first module, a second module, and a third module. The modules may be connected via Storm electrical cables (produced by Interconnect Systems of 1400 Memorex Drive, Santa Clara, Calif. 95050) having polyurethane jackets, ¼ inch Parker Push-Lok® hose (produced by Parker Hannifin Corporation of 30240 Lakeland Boulevard, Wickliffe, Ohio 44092), and fittings with 7/16-20 (size 4) JIC connections. Process fittings may be either yellow brass or 316L stainless steel for fluid compatibility.

The first module may include the motor controller, control switches, and associated connectors, relays, fuses, wires, etc., for controlling the motor 515. The motor controller may receive raw power and a 4 to 20 mA drive signal from a control system, and a signal from the level switch for the run-dry protection may also be received by the motor controller. The motor controller outputs regulated motor drive power and power for the level switch. The first module may be enclosed to protect against environmental hazards and electromagnetic interference.

The second module may include the pump 510, the motor operable to drive the pump 510, the run-dry protection, an air vent, a motor cover, and associated fittings and adaptors. The components may be arranged to reduce a total volume of the second module. The second module is operable to deliver a flow of the fluid to the third module for measurement.

The third module may include the measurement tube 410, the differential pressure sensor 440, the flow meter 490, the temperature sensor 500, the control unit 520, and associated piping, fittings, and hardware for mounting the components. The components of the third module may be mounted on heavy gauge stainless steel and enclosed with a sheet-metal cover. The third module may also include a vinyl cover. Electrical signals to and from the various components may be transmitted through a single, four pair, 18 gauge cable to the control unit 520.

The second and third modules may be located in close proximity to ensure a responsive viscosity measurement of the fluid, that is, to reduce a time delay between when the fluid is injected into the wellbore 20 and when a viscosity measurement is available. Once measured, the fluid may be discharged into a tank or flow line. The flow meter 490 may receive unregulated 24 volt DC power on one of the four pairs. The differential pressure sensor 440 and the temperature sensor 500 may be loop-powered 4 to 20 mA devices. The RMD 400 may also include a drain valve, such as on the pump 510 to drain a fluid being measured by the RMD 400, such as the fracturing fluid 110 or portion 230 thereof, or any other fluid. A portion of the measured fluid may collect in the RMD 400, such as the pump 510 after operation has stopped. Removal of the collected fracturing fluid 110 may prevent damage to the RMD 400, for example, damage caused by freezing of the measured fluid. The RMD 400 may also include a pressure relief device to prevent over-pressuring system components.

The above examples are merely illustrative and should not be construed to limit the scope of the present disclosure. Accordingly, other components and/or materials may be utilized to construct and/or implement the RMD and/or system of the present disclosure.

Figure 7:
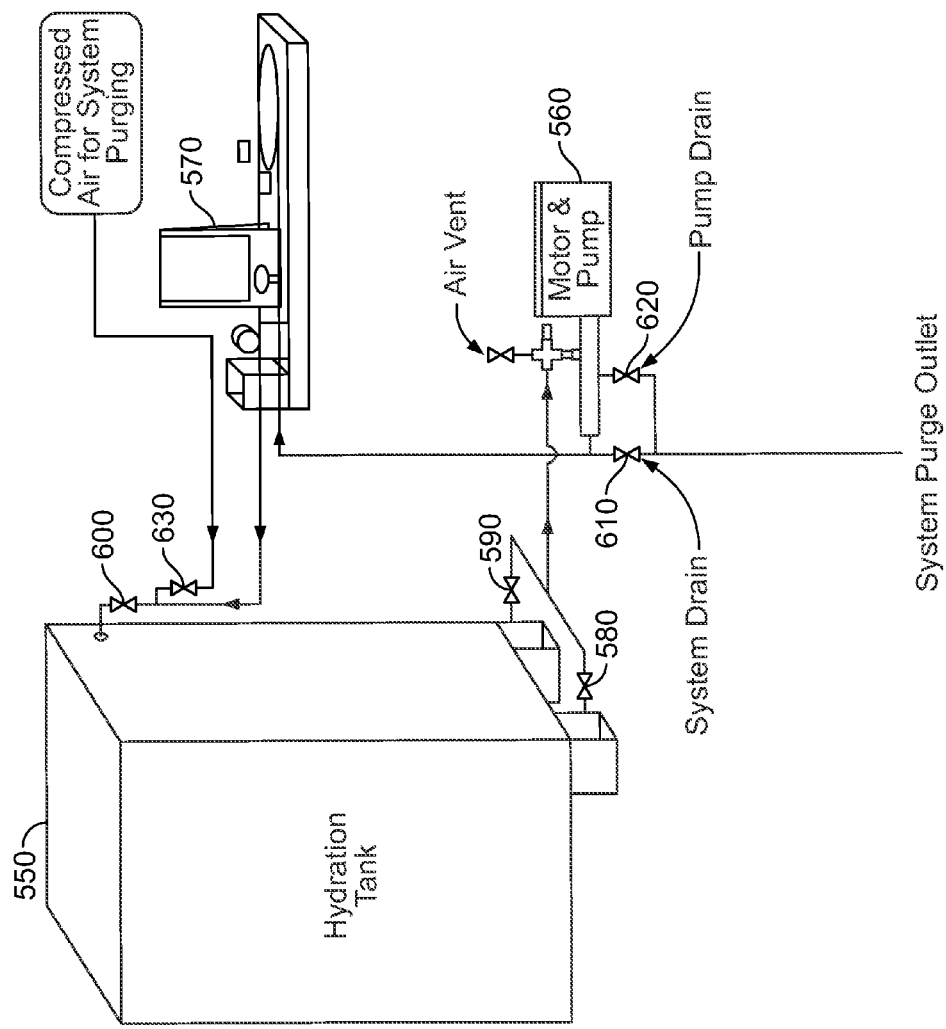
FIG. 7 is an example schematic diagram of an operating configuration of a rheology measuring device.

FIG. 7 shows a schematic diagram of an operating configuration of the RMD 400 including a hydration tank 550 in communication with both the second module 560 and the third module 570. The first module is not shown. The fluid being measured, such as the fracturing fluid 110, may be contained within the hydration tank 550 for a selected period of time. For example, the fracturing fluid 110 may be delivered to the hydration tank 550 and stored therein a predetermined period of time to allow the fracturing fluid 110 sufficient time to hydrate. Thereafter, a valve, such as one or more of valves 580 and 590, is opened. The second module 560 draws the fluid from the hydration tank 550 and, the fluid is directed to the third module 570, where the viscosity is measured. The fluid is then returned to the hydration tank 550 via a valve 600 that is normally open during measuring. Valves 610 and 620, which are normally closed during operation of the second and third modules 570 and 580, may be opened to purge fluid from the second module as well as conduits used to convey fluid from the hydration tank 550 to the second module 560 and from the second module to the third module 570. A valve 630 may also be opened to purge the fluid from the conduit used to return fluid from the third module 570 to the hydration tank 550.

FIG. 7 represents a configuration in which the fluid is being measured. However, according to another implementation, the fluid exiting the hydration tank 550 may be injected into a wellbore, such as wellbore 20, and a portion diverted to the third module 570 via the second module 560. The measured fluid may then be returned to the hydration tank 550 rather than being discarded.

In addition to determining a turbulent fluid's rheological properties, such as friction reduction, rheological properties of a laminar fluid, such as viscosity, may also be determined. According to some implementations, determination of a measured fluid's viscosity may be determined by the RMD 320, 330, and 400 using the following relationships:

According to some implementations, the fracturing fluid 110 is a non-Newtonian fluid. Thus, the viscosity for the fracturing fluid 110 may be determined by Equation 6, below, where $\gamma_w$ is the shear rate at the wall of the conduit conveying the fluid; $\gamma$ is a particular shear rate (such as a selected shear rate); $\mu_{app}$ is an apparent viscosity; and $\mu$ is a the viscosity at the particular shear rate $\gamma$. To solve Equation 6, the following steps may be utilized: (The steps are described with reference to FIG. 4 for illustration purposes.)

Step 1: A flow rate, Q, must be established through the measurement tube 410 at the desired Newtonian shear rate, $\gamma$.

Step 2: The pressure drop $\Delta P$ is measured, such as across locations 460 and 480.

Step 3: An estimate of the viscosity is determined utilizing the Equation 1 (below), where R is the radius of the measurement tube 410, L is the length of the measurement tube 410 between locations 460 and 480, Q is the flow rate of the fluid, and $K_1$ is the "K factor" or "meter factor."

Step 4: Estimate n (the power law coefficient) from the result of Step 3 using an established relationship of n versus viscosity and temperature.

Step 5: Calculate an improved estimate using Equation 3 (below) and n, previously determined.

Step 6: Re-estimate n from the result of Step 5 using any established relationship of n versus viscosity.

Step 7: Iterate Steps 5 and 6 until the viscosity converges within desired tolerances.

Step 8: Calculate the actual shear rate ($\gamma_w$) using Equation 4.

Step 9: Calculate the final viscosity at the desired shear rate ($\gamma$) using Equation 6.

$$\mu_{app} = \frac{\pi R^4 \Delta P}{8LQ} = K_1 \frac{\Delta P}{Q} \qquad \text{Equation 1}$$

$$\gamma_w = \frac{4}{\pi R^3} Q \qquad \text{Equation 2}$$

$$\mu_{app} = \frac{\pi R^4}{8LQ}\left(\frac{4n}{3n+1}\right) = K_1 \frac{\Delta P}{Q}\left(\frac{4n}{3n+1}\right) \qquad \text{Equation 3}$$

$$\gamma = \frac{4}{\pi R^3}\left(\frac{3n+1}{4n}\right) Q \qquad \text{Equation 4}$$

$$\mu_{app} = k(\dot{\gamma})^{n-1} \qquad \text{Equation 5}$$

$$\mu = \mu_{app}\left(\frac{\dot{\gamma}}{\dot{\gamma}_w}\right) \qquad \text{Equation 6}$$

Determination of the viscosity varies with temperature of the measured fluid. Thus, an additional fluid-specific adjustment may be performed to adjust the determined viscosity for a different temperature. Additionally, the calculated viscosity may be subject to correction, such as a rigorous, guar-based non-Newtonian fluid correction or a simple, guar-based non-Newtonian fluid correction. Most of the correction is performed to account for the bend geometry 542 of the measurement tube 410.

The rigorous correction involves modifying Equation 1 as follows:

$$\mu_{app} = K_{morgan} K_1 \frac{\Delta P}{Q} \qquad \text{Equation 7}$$

$K_{morgan}$ is a linear adjustment to the calculated viscosity. $K_{morgan}$ may be determined using Equations 8 and 9, shown below.

$$K_{morgan} = \frac{L}{L + \alpha N_{Re}^\beta} \qquad \text{Equation 8}$$

According to some implementations, alpha ($\alpha$) is equal to 0.0182, beta ($\beta$) is equal to 1.0678, and Re is the Reynolds number. The correction factor may vary from 0.80 to 0.99 for some tube geometries and measured fluids having viscosities in the range of 5 to 100 cP. The correction is considered rigorous because the Reynolds Number must be determined, which requires the determination of the measured fluid's density. If the density of the measurement fluid is not measured directly, such as with a densitometer, the density must be approximated, such as by a salt content of the base fluid 100. Further, determination of a Reynolds number requires knowledge of the measured fluid's viscosity, an approximation of which may only be known. Thus, determination of the correction factor may involve iteration and possibly other known numerical methods.

The simple correction involves correlating the performance of the RMD 400 with a known viscosity of the fluid by unitizing a simple addition or subtraction factor, such as 1.15. Therefore, the simple correction may be reflected in Equation 9, below:

$$\mu_{app} = K_1 \frac{\Delta P}{Q} - 1.15 \qquad \text{Equation 9}$$

A further correction may also be applied to correct for fluctuations in flow rate due to, for example, debris in the measured fluid or restrictions in the measuring tube 410 as a result thereof. The short-term perturbations in flow rate that may be experience may be corrected using Equation 10, below:

$$\mu_{app} = K_1 \frac{\Delta P}{Q}\left(\frac{Q_{ref}}{Q}\right)^{n-1} - 1.15 \qquad \text{Equation 10}$$

Equation 10 is operable to shift the viscosity from the measured flow rate to the desired flow rate, $Q_{ref}$, using power law fluid assumptions, and n is defined by the following relationship:

$$n = \text{MIN}(1, 1.77\mu^{-0.43}) \qquad \text{Equation 11}$$

Equation 11 may be used to estimate the power law coefficient n, and the MIN function represents, with respect to Equation 11, that the maximum values of n may not exceed 1.

The viscosity determination described above may be implemented as an application stored with and executed by the control unit 520 of the RMD 400. As a result, the RMD 400 is capable of determining the viscosity of the measured fluid, such as the base fluid 100, the fracturing fluid 110, or any other fluid, may be determined with high accuracy.

A number of implementations have been described. Nevertheless, it will be understood that various modifications may be made without departing from the spirit and scope of the disclosure. For example, implementations of the present disclosure may also be applicable to fluids flowing through pipelines. In order to reduce pumping requirements, such as for pumping the fluid up to a particular elevation, a friction reducer may be introduced into the fluid. Thus, implementations of the present disclosure may be used in a manner similar to that described above for pipeline applications. Accordingly, other implementations are within the scope of the following claims.

What is claimed is:

1. A method for controlling a well injection operation comprising:
   identifying a flow characteristic of a fracturing fluid;
   identifying a flow characteristic of a base fluid used for forming the fracturing fluid;
   determining an amount of friction reduction change of the fracturing fluid in relation to the flow characteristic of the fracturing fluid and the flow characteristic of the base fluid; and
   adjusting the amount of friction reduction of the fracturing fluid to coincide with a selected friction reduction amount.

2. The method according to claim 1, wherein identifying the flow characteristic of the fracturing fluid comprises measuring a pressure change of a flow of the fracturing fluid at a selected flow rate.

3. The method according to claim 2, wherein measuring the pressure change of the flow of the fracturing fluid at the selected flow rate comprises measuring the pressure change of the flow of the fracturing fluid at a flow rate corresponding to a flow rate at which the fracturing fluid is being injected into the well.

4. The method according to claim 1, wherein identifying the flow characteristic of the fracturing fluid comprises measuring a pressure change of a flow of the fracturing fluid at a one of a selected shear rate, Reynolds Number, fluid velocity, flow rate, or flow noise.

5. The method according to claim 1, wherein identifying the flow characteristic of the base fluid comprises measuring a pressure change of a flow of the base fluid at one of a selected shear rate, Reynolds Number, fluid velocity, flow rate, or flow noise.

6. The method according to claim 5, wherein measuring the pressure change of the flow of the base fluid at the selected flow rate comprises measuring the pressure change of the flow of the base fluid at a flow rate corresponding to a flow rate at which the fracturing fluid is being injected into the well.

7. The method according to claim 1, wherein identifying the flow characteristic of the base fluid used for forming the fracturing fluid comprises referencing a compilation of flow property data of the base fluid.

8. The method according to claim 7, wherein referencing a compilation of the flow property data of the base fluid comprises selecting from a plurality of predetermined flow characteristic data a flow characteristic value of the base fluid corresponding to a flow rate at which the fracturing fluid is being injected into the well.

9. The method according to claim 7, wherein referencing a compilation of the flow property data of the base fluid comprises selecting from a plurality of predetermined flow characteristic data a flow characteristic value of the base fluid at one of a selected shear rate, Reynolds Number, flow velocity, flow rate, or flow noise.

10. The method according to claim 1, wherein determining the amount of friction reduction change of the fracturing fluid comprises comparing a friction indicator of the base fluid to a friction indicator of the fracturing fluid.

11. The method according to claim 10, wherein comparing the friction indicator of the base fluid to the friction indicator of the fracturing fluid comprises comparing a predetermined pressure change of a flow of the base fluid at one of a selected shear rate, Reynolds Number, fluid velocity, flow rate, or flow noise to a pressure change of a flow of the fracturing flow at a corresponding one of the selected shear rate, Reynolds Number, fluid velocity, flow rate, or flow noise.

12. The method according to claim 10, wherein comparing the friction indicator of the base fluid to the friction indicator of the fracturing fluid comprises comparing a pressure change of a flow of the base fluid at one of a selected shear rate, Reynolds Number, fluid velocity, flow rate, or flow noise to a pressure change of a flow of the fracturing fluid at a corresponding one of the selected shear rate, Reynolds Number, flow velocity, flow rate, or flow noise.

* * * * *